United States Patent [19]

Szántay et al.

[11] 4,283,401
[45] Aug. 11, 1981

[54] PROCESS FOR THE PREPARATION OF 11-BROMO-VINCAMINIC ACID ESTER DERIVATIVES AND THEIR USE IN PROTECTING ANIMALS AGAINST CEREBRAL HYPOXY

[75] Inventors: Csaba Szántay; Lajos Szabó; György Kalaus; Lajos Dancsi; Tibor Keve; Egon Kárpáti; László Szporny, all of Budapest, Hungary

[73] Assignee: Richter Gedeon Vegyeszeti Gyar RT, Budapest, Hungary

[21] Appl. No.: 56,647

[22] Filed: Jul. 11, 1979

[30] Foreign Application Priority Data

Jul. 12, 1978 [HU] Hungary ................. RI 676
Jul. 12, 1978 [HU] Hungary ................. RI 677
Jul. 12, 1978 [HU] Hungary ................. RI 678

[51] Int. Cl.³ .................. A61K 31/55; C07D 459/00; C07D 461/00
[52] U.S. Cl. .................. 424/256; 260/239.3 P; 546/51; 546/70
[58] Field of Search .................. 260/239.3 P; 546/51, 546/70; 424/256

[56] References Cited

U.S. PATENT DOCUMENTS 3,770,724 11/1973 Warnant et al. ............. 260/239.3 P
4,146,643 3/1979 Pfäffli ..................... 546/51

*Primary Examiner*—Henry R. Jiles
*Assistant Examiner*—Robert T. Bond
*Attorney, Agent, or Firm*—Karl F. Ross

[57] ABSTRACT

A novel process for preparing 11-bromo-vincaminic acid esters of the general formula

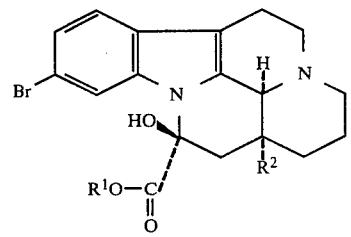

wherein $R^1$ and $R^2$ each stand independently from each other for a $C_{1-6}$ alkyl group, comprising the steps of treating a 1-alkyl-1-alkoxycarbonylethyl-octahydroindolo-quinolisine of the general formula

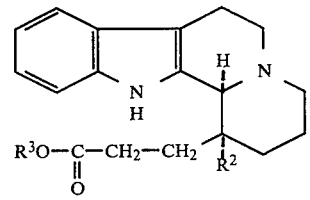

wherein $R^2$ is as defined above and $R^3$ stands for a $C_{1-6}$ alkyl group, with a brominating agent and treating the resulting isomeric mixture of the bromo-derivatives with an alkaline agent or treating the corresponding 14-oxo-E-homo-eburnane being unsubstituted in ring A with a brominating agent and nitrosating the resulting 11-bromo-14-oxo-E-homo-eburnane of the general formula

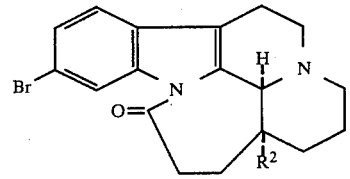

wherein $R^2$ is as defined above, then subjecting the resulting 11-bromo-14-oxo-15-hydroxyimino-E-homo-eburnanes to deoxyimination and treating the 14,15-dioxo-derivatives obtained with a base in an alcohol of the general formula $R^1OH$, wherein $R^1$ is as defined above.

All the intermediate products are novel and exhibit a therapeutical protecting effect against cerebral hypoxy.

30 Claims, No Drawings

PROCESS FOR THE PREPARATION OF 11-BROMO-VINCAMINIC ACID ESTER DERIVATIVES AND THEIR USE IN PROTECTING ANIMALS AGAINST CEREBRAL HYPOXY

This invention relates to a new process for the preparation of racemic or optically active 11-bromovincaminic acid esters of the formula (I),

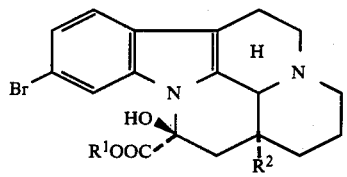

wherein $R^1$ and $R^2$ each represent a $C_{1-6}$ alkyl group, and the pharmaceutically acceptable acid addition salts thereof.

The above new compounds are prepared according to the invention as follows:

(a) an optically active 1-alkyl-1-alkoxycarbonylethyl-octahydroindoloquinolizine of the formula (II),

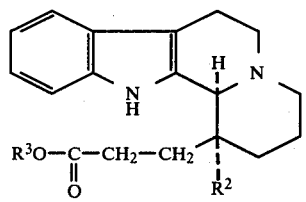

wherein $R^2$ is as defined above and $R^3$ is a $C_{1-6}$ alkyl group, or a racemate or a salt thereof is treated with a brominating agent, the resulting mixture of the respective new, optically active 10-bromo-1-alkyl-1-alkoxycarbonylethyl-octahydroindoloquinolizine of the formula (IIIa) and 8-bromo-1-alkyl-1-alkoxycarbonylethyl-octahydroindoloquinolizine of the formula (IIIb)

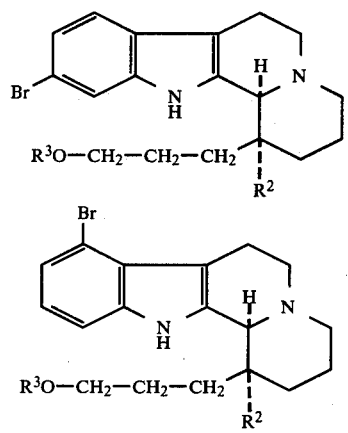

wherein $R^1$ and $R^2$ are as defined above, or of the corresponding racemates is treated with an alkaline agent, or (b) an optically active homoeburnane derivative of the formula (IV)

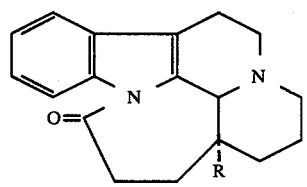

wherein R is as defined above, or a racemate thereof is treated with a brominating agent, and the 9- and 11-bromo-compounds are separated from the resulting mixture of the new optically active 11-bromo-14-oxo-E-homo-eburnane derivative of the formula (Va) and the new optically active 9-bromo-14-oxo-E-homo-eburnane derivative of the formula (Vb)

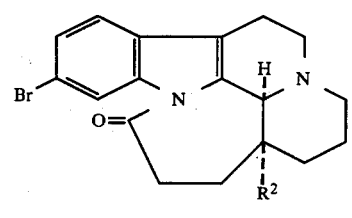

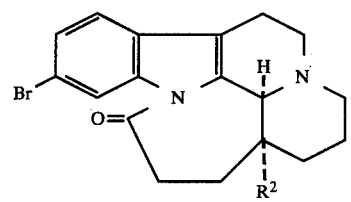

wherein $R^2$ has the above meaning, or from the mixture of the appropriate salts or racemates, and the thus-obtained racemic or optically active 11-bromo-14-oxo-E-homo-eburnane derivative of the formula (Va), wherein $R^2$ is as defined above, or an acid addition salt thereof is reacted with a nitrosating agent, the resulting racemic or optically active 11-bromo-14-oxo-15-hydroxyimino-E-homo-eburnane derivative of the formula (VI),

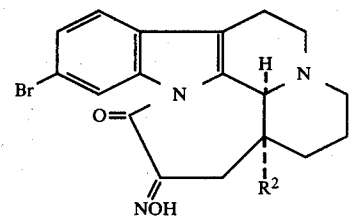

wherein $R^2$ is as defined above, or an acid-adition salt thereof is subjected to deoxyimination, the resulting racemic or optically active 11-bromo-14,15-dioxo-E-homoeburnane derivative of the formula (VII),

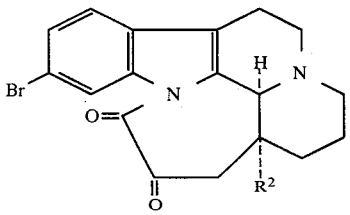

(VII)

wherein R² is as defined above, or an acid addition salt thereof is treated with a base in an alcohol of the formula R¹OH, wherein R¹ is as defined above, and, if desired, the resulting 11-bromo-vincaminic acid ester of the formula (I) is converted into its pharmaceutically acceptable acid addition salt.

If a racemic 11-bromo-14-oxo-E-homo-eburnane derivative of the formula (II) is used as the starting substance in the above process and an optically active endproduct of the general formula (I) is to be prepared, any of the above intermediates having the formulae (III), (IV), (Va), (Vb), (VI) and, resp., (VII), or the end product itself can be resolved to form the appropriate pure optically active isomers.

In the above formulae R¹ and R² may stand for straight-chained or branched $C_{1-6}$ alkyl groups, such as methyl, ethyl, n-propyl, isopropyl, n-butyl, isobutyl, sec.-butyl, tert.-butyl, n-pentyl, isopentyl, n-hexyl and isohexyl groups.

The 11-bromo-vincaminic acid esters of the formula (I) prepared according to the invention possess valuable therapeutical properties. These compounds can be applied in the treatment of behavioural disorders originating from senile cerebrovascular damages and sclerosis, as well as in the therapy of disorientations following cranial injuries.

The German patent specification No. 2,458,164 reports on the preparation of some representatives of the 11-bromo-vincaminic acid esters having the general formula (I). According to this known method 3-(1-ethyl-10-bromo-octahydroindoloquinolizine-1-yl)-2-methoxypropenic acid methyl ester is treated with an acid to yield a mixture of 11-bromo-vincamine and 11-bromo-apovincamine. At the end of the reaction 11-bromo-vincamine should be separated from the by-product in an additional step. The starting substance of the above process is prepared from ethyl-(3([p-toluenesulfonyloxy]-prop-1-yl)-malonaldehyde acid diacetal and the appropriate bromotryptamine by a five-step synthesis, through complicated intermediates. The cited patent specification also discloses a process for the preparation of 11-bromo-vincamine by the direct bromination of vincamine, without indicating, however, the yield of the end product. According to our experiments no satisfactory yield can be attained by this latter method.

The 11-bromo-vincaminic acid esters and their homologs can be prepared according to the process of the invention from new, easily available starting substances in five easily performable reaction steps through simple intermediates. The process of the invention provides the end products in high yields and in pure state, free from the respective 11-bromo-apovincaminic acid esters.

The optically active compounds of the formula (II), used as starting substances in the process variant (a) of the invention, can be prepared as described in the Hungarian patent application No. RI-633 by resolving the appropriate 1-alkyl-1-alkoxy-carbonylethyl-octahydroindoloquinolizine compounds.

The starting substances of the formula (II) are brominated preferably with elementary bromine, but other conventional brominating agents, such as N-bromosuccinimide, can be used as well.

Bromination is performed in the presence of an inert solvent or solvent mixture. As solvents e.g. apolar organic liquids, such as halogenated aliphatic hydrocarbons, e.g. chloroform, dichloromethane, etc., furthermore polar organic liquids, such as organic acids, e.g. glacial acetic acid, etc., can be used. In some instances a small amount of a second solvent, such as an aliphatic alcohol, e.g. methanol, can also be added to the main solvent, for instance, to glacial acetic acid, thereby conducting the reaction in a solvent mixture.

When bromination is performed in an apolar organic solvent, such as in a halogenated aliphatic hydrocarbon, it is preferred to add a Lewis acid to the reaction mixture. As the Lewis acid e.g. ferric chloride, zinc chloride, aluminum chloride, stannic chloride, boron trifluoride, etc. can be used.

Bromination is performed preferably at room temperature. The reaction proceeds within about 0.5 to 2 hours; it is generally complete within about one hour.

When brominating a compound of the formula (II), a mixture of the appropriate compounds of the formulae (IIIa) and (IIIb) is obtained as product. These two structural isomers can be separated from each other by methods known per se, such as by fractional crystallization, salt formation and separation of the salts, preparative layer chromatography, etc. When the isomers are separated from each other by preparative layer chromatography, it is preferred to use silica gel (e.g. Merck $PF_{254+366}$ grade silica gel) as adsorbent; various solvent mixtures, such as mixtures of benzene and methanol, can be utilized as eluting agent.

It is, however, not necessary to separate from each other the isomeric bromine compounds of the formulae (IIIa) and (IIIb) at this stage of the synthesis and to treat them separately in the subsequent step. It is far more preferable to treat the isomeric mixture itself with an alkaline agent first, and to separate from each other only the 9-bromo- and 11-bromo-E-homo-eburnane derivatives formed in this latter step.

When converting the compounds of the formulae (IIIa) and (IIIb) into the desired end products, it is preferred to use an alkali hydride, such as sodium hydride, or an alkali tert.-alkoxide, such as lithium, potassium or sodium tert.-butoxide, as alkaline agent. An aromatic hydrocarbon, such as benzene or toluene, can be used as the reaction medium.

The compounds of the formula (IV), utilized as starting substances in the process variant (b) of the invention, can be prepared by treating the respective 1-alkyl-1-alkoxy-carbonylethyl-octahydroindoloquinolizine derivatives with an alkali. This method is disclosed in the Hungarian patent specification No. 163,769.

The starting substances of the formula (II) are brominated preferably with elementary bromine, but other known brominating agents, such as N-bromosuccinimide, can also be used for this purpose.

Bromination is performed in the presence of an inert solvent or solvent mixture. As solvents e.g. apolar organic liquids, such as halogenated aliphatic hydrocarbons, e.g. chloroform, dichloromethane, etc., furthermore polar organic liquids, such as organic acids, e.g. glacial acetic acid, can be used. In some instances a small amount of a second solvent, such as an aliphatic alcohol, e.g. methanol, can also be added to the main solvent, for instance, to glacial acetic acid, thereby conducting the reaction in a solvent mixture.

When bromination is performed in an apolar organic solvent, such as in a halogenated aliphatic hydrocarbon, it is preferred to add a Lewis acid to the reaction mixture. As Lewis acid e.g. ferric chloride, zinc chloride, aluminum chloride, stannic chloride, boron trifluoride, etc. can be applied.

Bromination is performed preferably at room temperature. The reation proceeds generally within about 0.5 to 2 hours; in most of the instances it is complete within about one hour.

When subjecting a compound of the formula (II) to bromination, an isomeric mixture consisting of the bromo derivatives of the formulae (Ia) and (Ib) is obtained as reaction product. These structural isomers can be separated from each other by methods known per se, such as by salt formation, selective crystallization, preparative layer chromatography, etc. When separation is performed by preparative layer chromatography, it is preferred to use silica gel (such as Merck $PF_{254-366}$ grade silica gel) as an adsorbent; various solvent mixtures, such as mixtures of benzene and methanol, can be utilized as eluting agents.

According to the process of the invention the starting substances of the formula (Va) are nitrosated preferably with a tertiary alkylnitrite in the presence of an alkaline agent, such as an alkali metal alkoxide, particularly lithium, sodium or potassium tert.butoxide. The reaction is performed in the presence of an inert solvent, such as in an aromatic hydrocarbon, e.g. benzene, toluene, etc. The resulting compounds of the formula (VI) can be converted into their acid addition salts by methods known per se. If desired, the racemic mixtures of these compounds can be resolved to yield the pure optically active isomers.

The intermediates of the formula (VI) can be deoxyiminated by reductive methods, e.g. by treatment with zinc in aqueous acetic acid, by oxidative methods, e.g. by treatment with thallium nitrate, or by a so-called transoximation method, e.g. by treatment with an acid in the presence of a carbonyl compound.

According to this latter, particularly preferred method the compounds of the formula (VI) are dissolved in an organic acid and treated with paraformaldehyde in the presence of an aromatic sulfonic acid. As organic acid, e.g. a $C_{1-6}$ alkanecarboxylic acid, such as formic acid, acetic acid, etc., can be used. Of the aromatic sulfonic acids usable in this reaction p-toluenesulfonic acid is to be mentioned. If desired, the resulting compounds of the formula (VII) can be converted into their acid addition salts by methods known per se, and/or the racemates can be resolved in a conventional way to yield the pure optically active isomers.

In the last step of the synthesis according to the invention the compounds of the formula (VII) are treated with a base, preferably with an alkali metal alkoxide, such as lithium, potassium or sodium tert.-butoxide, in the presence of an alcohol of the formula $R^1$—OH corresponding to the ester to be prepared. This step yields the required end products of the formula (I).

The reaction mixtures formed in the individual steps of the above synthesis can be processed by conventional methods. Depending on the nature of the compound and of the solvent used, the intermediates or the end-products can be isolated from the reaction mixture e.g. by filtration or by evaporating the solvent optionally under reduced pressure. If desired, the isolated substances can be purified by recrystallization from an appropriate inert organic solvent. The solvents to be utilized for this purpose are selected in accordance with the solubility conditions and crystallization properties of the compounds in question. The reaction mixtures can also be processed by extracting the product from the mixture with an appropriate inert organic solvent, such as dichloromethane, dichloroethane, etc., drying and evaporating the solution, and, if necessary, crystallizing the residue from an appropriate solvent. In some instances the product can also be precipitated from the reaction mixture with an appropriate inert organic solvent, such as ether, and isolated by filtration. If desired, the resulting racemic or optically active compounds can be purified further by additional conventional operations, such as by recrysallization.

The products obtained by the process of the invention can also be purified by preparative layer chromatography. For this purpose it is preferred to use silica gel, such as the Merck $PF_{254+366}$ grade silica gel, as adsorbent; various solvent mixtures can be utilized as the eluting agent.

If desired, the racemic or optically active compounds of the formulae (I), (IIIa), (IIIb), (Va), (Vb), (VI) and (VII) obtained according to the method of the invention can be converted into their pharmaceutically acceptable acid addition salts by reacting the free bases with appropriate acids. Examples of the acids applicable for this purpose are mineral acids, such as hydrohalic acids, e.g. hydrochloric acid, hydrobromic acid, etc., sulfuric acid, phosphoric acid and perhaloic acids, e.g. perchloric acid; furthermore organic carboxylic acids, such as formic acid, acetic acid, propionic acid, oxalic acid, glycolic acid, maleic acid, fumaric acid, succinic acid, tartaric acid, ascorbic acid, citric acid, malic acid, salicylic acid, lactic acid, benzoic acid or cinnamic acid; sulfonic acids, such as methanesulfonic acid, p-toluenesulfonic acid or cyclohexylsulfonic acid; and amino acids, such as aspartic acid, glutamic acid, N-acetyl-aspartic acid, N-acetyl-glutamic acid, etc.

The salt formation is performed preferably in an inert solvent, particularly in an aliphatic alcohol, such as methanol, by dissolving the free base of the formulae (I), (IIIa), (IIIb), (Va), (Vb), (VI), or (VII) in the solvent and acidifying the solution slightly (to about pH=6) with the selected acid. The resulting salt separates from the reaction mixture, or it can be precipitated with an appropriate organic solvent, such as ether.

The compounds of the formula (I), (IIIa), (IIIb), (Va), (Vb), (VI) and (VII) contain asymmetric carbon atoms, consequently they can exist in the form of optically active isomers and racemic mixtures. The process of the invention also encompasses the preparation of the optically active antipodes of the end-products. The optically active compounds of the formula (I), (IIIa) (IIIb), (Va), (Vb), (VI) and (VII) can be prepared either by resolving the corresponding racemic mixtures in a manner known per se, or by utilizing optically active compounds of the formula (II) or (IV) as starting substances. According to a third method, the synthesis is started with a racemic compound of the formula (II) or (IV), one of the resulting racemic intermediates is resolved, and the subsequent steps of the synthesis are performed on the optically active intermediates. If desired, any of the optically active compounds prepared according to the invention can be converted into the respective racemic mixtures by methods known per se.

The compounds of the formula (I) can be prepared according to the method of the invention in high yields as easily identifiable pure substances. The analytical data of the products are in good agreement with the calculated ones, and the characteristic IR, NMR and mass spectral peaks of the compounds confirm the assigned structures.

The compounds of the formulae (IIIa), (IIIb), (Va), (Vb), (VI) and (VII), formed as intermediates in the process of the invention, are new substances possessing biological activities. These new compounds, as well as their preparation are also embraced by the scope of the invention. Furthermore, the invention also encompasses the methods in which one of the above intermediates is applied as starting substance and only the remaining steps of the synthesis are carried out, or in which the intermediates formed in the individual steps are not isolated, and the next step of the reaction is performed directly on the mixtures containing the intermediates in question.

The novel intermediate products of the invention were subjected to pharmacological tests. It has been found that particularly compounds of the formulae Va, Vb and VI possess considerable pharmacological activity. The tests were carried out according to the method described below:

Survival time of mice with normobaric hypoxy 5 male mice were put into a cylindrical glass vessel of 3 liters volume through which a gas mixture containing 96% of nitrogen and 4% of oxygen was streamed. The time from putting the mice into the glass vessel until their decrease was measured and those of the animals were considered as protected which were alive after elapse of the double survival time of the untreated control animals. The compounds to be tested were intraperitoneally administered in doses of 50 mg. per kg. of body weight to 10 animal each 30 minutes before putting them into the glass vessel.

The test results are summarized in the following Table:

| Compound | Survival time Average ± deviation, minutes | % | Protective effect % |
|---|---|---|---|
| Control | 5.4 ± 0.96 | — | 0 |
| (X1X) | 7.5 ± 3.14 | +39 | 10 |
| (X2X) | 6.7 ± 1.44 | +24 | 0 |
| (X3X) | 6.5 ± 3.20 | +20 | 10 |
| Control | 6.3 ± 1.45 | — | 0 |
| Vincamine | 7.1 ± 1.30 | +13 | 0 |

Compounds:
(X1X)3(S),17(S)-11-Bromo-14-oxo-E-homo-eburnane
(X2X)3(S),17(S)-9-Bromo-14-oxo-E-homo-eburnane
(X3X)3(S),17(S)-11-Bromo-14-oxo-15-hydroxyimino-E-homo-eburnane hydrochloride It is shown by the data of the Table that the survival time of the animals with hypoxy caused by reducing the oxygen content of the atmosphere has been considerably extended by the administration of the novel compounds tested. This extension amounts in average to 20-40% of the survival time of the untreated control animals; in one case the survival time was even doubled. The effect of the novel compounds exceeds the effect of vincamine, at present successfully used in the therapy, which known compound extended in average only by 13% the survival time of animals under the same conditions and with the same doses; in the case of vincamine, however, the survival time never was doubled.

The protecting effect of the novel compounds according to the invention against cerebral hypoxy can be utilized in every case where the oxygen supply of the brain has been reduced by the damages of the cerebral blood circulation.

The invention is elucidated in more detail by the aid of the following non-limiting Examples.

EXAMPLE 1

Preparation of a mixture of
1(S),12b(S)-1-ethyl-1-(2'-methoxycarbonylethyl)-10-bromo-1,2,3,4,6,7,12,12b-octahydroindolo[2,3-a]quinolizinium hydrochloride and
1(S),12b(S)-1-ethyl-1-(2'-methoxycarbonylethyl)-8-bromo-1,2,3,4,6,7,12,12b-octahydroindolo[2,3-a]quinolizinium hydrochloride 6.99 g (10 mmoles) of (−)-1(S),12b(S)-ethyl-1-(2'-methoxycarbonylethyl)-1,2,3,4,6,7,12,12b-octahydroindolo[2,3-a]quinolizine dibenzoyl-D-tartrate are shaken with a mixture of 80 ml. of dichloromethane and 10 ml. of 10% aqueous ammonium chloride solution. The organic phase is separated, dried over 10 g. of anhydrous sodium sulfate, and filtered. 0.1 g. of dry ferric chloride are added to the filtrate, and then 0.67 ml. (2.08 g, 13 mmoles) of bromine are added dropwise to the mixture at 25° C. under vigorous stirring. When the addition is complete, the mixture is stirred for additional 3 hours at room temperature, and then it is rendered alkaline with 5 ml. of 10% aqueous ammonia. The precipitated ferric hydroxide is filtered off, the dichloromethane phase of the filtrate is separated, dried over 10 g. of anhydrous sodium sulfate, and then filtered. 10 ml. of methanol and 2 ml. of 5% methanolic hydrochloric acid are added to the filtrate, and dichloromethane is evaporated in vacuo. A mixture of (1S),12b(S)-1-ethyl-1-(2'-methoxycarbonylethyl)-1o-bromo-1,2,3,4,6,7,12,12b-octahydroindolo[2,3-a]-quinolizinium hydrochloride and 1(S),12b(S)-1-ethyl-1-(2'-methoxycarbonylethyl)-8-bromo-1,2,3,4,6,7,12,12b-octahydroindolo[2,3-a]quinolizinium hydrochloride separates from the residue in crystalline form. 3.2 g. (70%) of the salt mixture, containing the 10-bromo and 8-bromo derivatives in a weight ratio of 60:40 to 40:60, are obtained; m.p.: 234°-236° C.

EXAMPLE 2

Preparation of
3(S),17(S)-11-bromo-14-oxo-E-homoeburnane and
3(S),17(S)-9-bromo-14-oxo-E-homo-eburnane 4.56 g. (10 mmoles) of the salt mixture obtained as described in Example 1 are shaken with a mixture of 40 ml. of dichloromethane and 5 ml. of 10% aqueous ammonia. The organic phase is separated, dried over anhydrous sodium sulfate, filtered, and the filtrate is evaporated. The oily residue is dissolved in 330 ml. of abs. toluene, and about 30 ml. of toluene are distilled off until the head temperature reaches 107° C. The residue is cooled, 2.4 g (30 mmoles) of lithium-tert.-butoxide are added, and the mixture is stirred at room temperature for 60 hours. Thereafter the toluene solution is admixed with 50 ml. of 2.5% by volume of aqueous sulfuric acid under cooling, the aqueous phase is removed, and the organic phase is extracted twice more with 20 ml. each of 2.5 v/v % aqueous sulfuric acid. The aqueous phases are combined, admixed with 100 ml. of dichloromethane, and the pH of the aqueous phase is adjusted to 9 with concentrated aqueous ammonia under cooling and stirring. The organic phase is separated, and the aqueous phase is extracted with 30 ml. of dichloromethane. The organic solutions are combined, dried over 10 g. of anhydrous sodium sulfate, filtered, and the filtrate is evaporated to an oil. This oily residue solidifies upon standing. In this way 1.5 g. (40%) of a substance melting at 76°–82° C. are obtained; this substance is a mixture of 3(S),17(S)-11-bromo-14-oxo-E-homo-eburnane and 3(S),17(S)-9-bromo-14-oxo-E-homo-eburnane.

The components of the resulting mixture are separated from each other by preparative layer chromatography (adsorbent: silica gel Merck KG-PF$_{254+366}$; solvent: a 14:3 mixture of benzene and methanol; eluting agent: a 20:4 mixture of dichloromethane and methanol). The $R_f$ value of the 9-bromo compound is higher than that of the 11-bromo derivative.

0.9 g. (60%) of 3(S),17(S)-11-bromo-14-oxo-E-homo-eburnane are isolated from the band with lower $R_f$ value. This compound melts at 122°–123° C. after recrystallization from a mixture of isopropanol and dichloromethane. $[\alpha]_D^{20} = +13.1°$ (c=2.06, in dimethyl formamide).

IR spectrum (in KBr pellets): 1706 cm$^{-1}$ (lactam CO).

Mass spectrum: m/e (%)=386 (M$^+$, 100), 385 (56), 358 (5.0) 357 (8.9), 344 (2.6), 343 (3.4), 330 (11), 329 (8.1), 315 (4.8), 308 (4.8), 307 (5.0), 306 (1.5), 261 (4.0), 248 (4.4).

$^1$H-NMR (DMSO-d$_6$, CDCl$_3$): δ=8.56 (1H, 12-H), 7.32 (2H, 9H and 10H), 4.10 (1H, s, 3-H), 0.88 (3H, t, —CH$_2$CH$_3$) ppm.

0.4 g. (40%) of 3(S),17(S)-9-bromo-14-oxo-E-homo-eburnane are isolated from the band with higher $R_f$ value. This compound melts at 154°–156° C. after recrystallization from a mixture of methanol and dichloromethane.

$[\alpha]_D^{20} = +31.5°$ (c=1, in dimethyl formamide).

IR spectrum (in KBr pellets): 1712 cm$^{-1}$ (lactam CO).

Mass spectrum: m/e (%)=386 (M$^+$, 100), 385 (72), 358 (15), 357 (15), 344 (7.2), 343 (7.5), 330 (22), 329 (20), 317 (11), 315 (11), 304 (3.5), 303 (5.0), 302 (3.2), 301 (5.0), 248 (11).

$^1$H-NMR (CDCl$_3$+DMSO-d$_6$): δ=8.50–7.00 (3H, m, aromatic protons), 4.03 (1H, s, 3-H), 0.85 (3H, t, —CH$_2$CH$_3$) ppm.

EXAMPLE 3

Preparation of
3(S),17(S)-11-bromo-14-oxo-E-homo-eburnane and
3(S),17(S)-9-bromo-14-oxo-E-homo-eburnane One proceeds as described in Example 2, with the difference that the resulting 1.5 g. of the mixture of the 9-bromo and 11-bromo compounds are recrystallized from 2 ml. of acetonitrile. 0.9 g. of crystalline 3(S),17(S)-11-bromo-14-oxo-E-homo-eburnane are obtained; the physical constants of this compound are the same as given in Example 2 for the 11-bromo derivative.

The mother liquor obtained in the crystallization step is processed by preparative layer chomatography as described in Example 2 (adsorbent: silica gel Merck KG-PF$_{254+366}$; solvent: a 14:3 mixture of benzene and methanol; eluting agent: a 20.4 mixture of dichloromethane and methanol). In this way 0.4 g. of 3(S),17(S)-9-bromo-14-oxo-E-homo-eburnane are obtained with the same physical constants as given in Example 2 for the 9-bromo compound.

EXAMPLE 4

3(S),17(S)-11-Bromo-14-oxo-E-homo-eburnane 1.00 g. (3.24 mmoles) of 3(S),17(S)-14-oxo-E-homo-eburnane is dissolved in 5 ml. of chloroform, and 1.00 g. (3.68 mmoles), of ferric chloride hexahydrate is added to the solution. The mixture is cooled to 0° C., and a solution of 0.75 g. (4.68 mmoles) of bromine in 5 ml. of chloroform is added dropwise to the stirred mixture. Stirring is continued at 0° C. for additional 5 hours. The mixture is allowed to stand in a refrigerator overnight, thereafter a solution of 0.20 g. (1.25 mmoles) of bromine in 1 ml. of chloroform is added, and the mixture is stirred again at 0° C. for 5 hours. Thereafter the mixture is rendered alkaline by introducing 8 ml. of a 1:1 mixture of concentrated aqueous ammonia and water. The separated precipitate is removed by filtration from the resulting two-phase mixture, the filtrate is washed with dichloromethane, the phases are separated from each other, and the aqueous phase is extracted again with dichloromethane. The organic phases are combined, dried over anhydrous magnesium sulfate, filtered, and the filtrate is evaporated in vacuo. The residue is subjected to preparative layer chromatography (adsorbent: silica gel Merck PF$_{254+366}$; solvent: a 20:1 mixture of dichloromethane and methanol; eluting agent: a 2:4 mixture of dichloromethane and methanol). 0.10 g. (10%) of non-reacted starting substance are isolated from the first band with lower $R_f$ value, whereas the processing of the second band with higher $R_f$ value yields 0.75 g. of a mixture of the 11-bromo and 9-bromo isomers. This isomeric mixture is subjected to a second separation step by preparative layer chromatography (adsorbent: silica gel Merck PF$_{254+366}$; solvent: a 14:3 mixture of benzene and methanol; eluting agent: a 20:4 mixture of dichloromethane and methanol). In this latter step 0.53 g. (42.5%) of 3(S),17(S)-11-bromo-14-oxo-E-homo-eburnane can be isolated from the first band with lower $R_f$ value; the product melts at 122°–123° C. after recrystallization from a mixture of isopropanol and dichloromethane.

IR (in KBr pellets): 1706 cm$^{-1}$ (lactam CO).

Mass spectrum: m/e (%)=386 (M$^+$, 100), 385 (56), 358 (5.0), 357 (8.9), 344 (2.6), 343 (3.4), 330 (11), 329 (8.1), 315 (4.8), 307 (5.0), 306 (1.5), 261 (4.0), 248 (4.4)

$^1$H-NMR (DMSO-d$_6$, CDCl$_3$): δ=8.56 (1H, 12-H), 7.32 (2H, 9-H and 10H), 4.10 (1H, s, 3-H), 0.88 (3H, t, —CH$_2$CH$_3$) ppm.

$[\alpha]_D^{20} = +13.1°$ (c=2.06, in dimethyl formamide).

71 mg. (5.6%) of 3(S),17(S)-9-bromo-14-oxo-E-homo-eburnane are isolated from the second band with higher $R_f$ value. This compound melts at 154°–156° C. after recrystallization from a mixture of methanol and dichloromethane.

IR (in KBr pellets): 1712 cm$^{-1}$ (lactam CO).

Mass spectrum, m/e (%)=386 (M$^+$, 100), 385 (72), 358 (15), 357 (15), 344 (7.2), 343 (7.5), 330 (22), 329 (20), 317 (11), 315 (11), 304 (3.5), 303 (5.0), 302 (3.2), 301 (5.0), 248 (11).

$^1$H-NMR (CDCl$_3$+DMSO-d$_6$): δ=8.50–7.00 (3H, aromatic protons), 4.03 (1H, s, 3-H), 0.85 (3H, t, —CH$_2$CH$_3$) ppm.

$[\alpha]_D^{20} = 31.5°$ (c=1.236, in dimethyl formamide).

EXAMPLE 5

(±)-Cis-11-bromo-14-oxo-E-homo-eburnane-(3α,17α)

One proceeds as described in Example 1 with the difference that 3(S),17(S)-14-oxo-E-eburnane is replaced by the same amount of (±)-cis-14-oxo-E-homo-eburnane-(3α,17α). In this way 0.55 g. of (±)-cis-11-bromo-14-oxo-E-homo-eburnane-(3α,17α) are obtained; m.p.: 154° C. (decomposition).

EXAMPLE 6

3(S),17(S)-11-Bromo-14-oxo-E-homo-eburnane 5.00 g. (16.2 mmoles) of 3(S),17(S)-14-oxo-E-homo-eburnane are dissolved in 25 ml. of chloroform, and 5.00 g. (18.4 mmoles) of ferric chloride hexahydrate are added to the solution. The mixture is cooled to 0° C., and a solution of 3.75 g (23.4 mmoles) of bromine in 25 ml. of chloroform is added dropwise to the stirred mixture. Stirring is continued at 0° C. for additional 5 to 8 hours, and then the mixture is allowed to stand in a refrigerator at 5° C. overnight. The progress of the reaction is monitored by thin layer chromatography (adsorbent: silica gel; solvent: a 20:1 mixture of dichloromethane and methanol; the $R_f$ value of the brominated end-product is higher than that of the starting substance).

The mixture is rendered alkaline with 40 ml. of a 1:1 mixture of concentrated aqueous ammonia and water. The separated precipitate is removed by filtration from the resulting two-phase mixture, and the filter cake (ferric hydroxide) is washed with dichloromethane. The phases of the filtrate are separated from each other, and the aqueous phase is extracted with dichloromethane. The organic phases are combined, dried over anhydrous magnesium sulfate, filtered, and the filtrate is evaporated in vacuo. The oily residue is crystallized from 8 ml. of acetonitrile. The crystals are separated by filtration, washed with a small amount of cold acetonitrile and dried. In this way 2.10 g. (33.4%) of 3(S),17(S)-11-bromo-14-oxo-E-homo-eburnane are obtained, the physical constants of which are identical with those of the 11-bromo isomer obtained according to Example 4.

The acetonitrile mother liquor obtained in the crystallization step is evaporated to dryness in vacuo, and the residue is processed by preparative layer chromatography as described in Example 4 (adsorbent: silica gel Merck KG-PF$_{254+366}$; solvent: a 14:3 mixture of benzene and methanol; eluting agent: a 20:4 mixture of dichloromethane and methanol). The physical constants of 3(S),17(S)-9-bromo-14-oxo-E-homo-eburnane, isolated from the eluate, are identical with those of the 9-bromo isomer obtained according to Example 4.

EXAMPLE 7

3(S),17(S)-11-Bromo-14-oxo-15-hydroxyimino-E-homo-eburnane hydrochloride 0.27 g. (0.69 mmoles) of 3(S),17(S)-11-bromo-14-oxo-E-homo-eburnane are suspended in 1.7 ml. of abs. toluene. The suspension is stirred under a nitrogen atmosphere, and 0.65 ml. of tert.-butyl nitrite, followed by a suspension of 0.20 g. of potassium tert.-butoxide in 1.7 ml. of abs. toluene are added. The reaction mixture is stirred at room temperature and under exclusion of atmospheric moisture for one hour. The progress of the reaction can be monitored by thin layer chromatography utilizing silica gel (e.g. Merck KG-G grade silica gel) as adsorbent and a 14:3 mixture of benzene and methanol as eluting agent, on the basis that the $R_f$ value of the product is higher than that of the non-reacted starting substance. A solution of 0.54 g. of ammonium chloride in 10 ml. of water is added then to the mixture, and the two-phase mixture is stirred for 10 minutes. The toluene phase is separated, and the aqueous phase is shaken thrice with 5 ml. of dichloromethane each. The organic solutions are combined, dried over anhydrous magnesium sulfate, filtered, and the filtrate is evaporated in vacuo. The residue, weighing 0.23 g., is dissolved in a mixture of 1 ml. of methanol and 0.2 ml. of dichloromethane, and the pH of the solution is adjusted to 5 with methanolic hydrochloric acid. The separated product is filtered off, washed with a small amount of cold methanol, and dried. In this way 0.16 g. (51%) of 3(S),17(S)-11-bromo-4-oxo-15-hydroxyimino-E-homo-eburnane hydrochloride are obtained; m.p.: 235° C. (decomposition).

IR (in KBr pellets): 3460 (OH), 1710 (lactam CO) and 1622 (C=N) cm$^{-1}$.

Mass spectrum: m/e (%)=415 (M$^+$, 62), 414 (42), 399 (22), 398 (29), 385 (100), 370 (60), 358 (14), 356 (7.0), 341 (14), 329 (21), 317 (8.4), 315 (11), 249 (14), 141 (20).

$[\alpha]_D^{20} = +45.6°$ (c=1.14, in dimethyl formamide).

EXAMPLE 8

3(S),14(S),16(S)-11-Bromo-vincamine 0.20 g. of dry p-toluenesulfonic acid and 0.30 g. of paraformaldehyde are added to a solution of 0.10 g. (0.22 mmoles) of 3(S),17(S)-11-bromo-14-oxo-15-hydroxyimino-E-homo-eburnane hydrochloride in 2 ml. of glacial acetic acid, and the mixture is stirred at 110° C. under exclusion of atmospheric moisture for 3 hours. Thereafter the reaction mixture is poured onto ice, and the resulting mixture is rendered alkaline (to pH=9) with concentrated aqueous ammonia, whereupon the product precipitates. In this way 86 mg. of 3(S),17(S)-11-bromo-14,15-dioxo-E-homo-eburnane are obtained; m.p.: 144°–146° C. (after recrystallization from ether).

IR (in KBr pellets): 1720 (CO), 1690 (acid amide CO) cm$^{-1}$. The resulting product is used in the next step without purification.

0.10 g. of potassium tert.-butoxide are dissolved in 3.0 ml. of abs. methanol. 0.3 ml. of the resulting solution are added to the crude 3(S),17(S)-11-bromo-14,15-dioxo-E-homo-eburnane obtained as described above, the mixture is warmed to 40° C., and then it is allowed to stand at room temperature for 2 hours. The separated crystals are collected by filtration, washed with cold methanol and dried. In this way 28 mg. of 3(S),14(S),16(S)-11-bromovincamine are obtained; m.p. 207°–208° C. (decomposition). No melting point decrease occurs when admixing this product with an authentic sample of the same compound.

IR (in KBr pellets): 1742 (ester CO), 1610 (aromatic) cm$^{-1}$.

Mass spectrum: m/e (%)=432 (M$^+$, 95.6), 431 (34), 417 (9.2), 385 (17.5), 373 (34), 345 (48), 330 (61).

$^1$H-NMR (CDCl$_3$): δ=7.41–7.18 (3H, m, aromatic protons), 4.52 (1H, replaceable, OH), 3.83 (3H, s, —COOCH$_3$ ), 0.90 (3H, t, —CH$_2$CH$_3$) ppm.

The methanolic mother liquor is purified by preparative layer chromatography, taking into account that the $R_f$ values decrease in the order of end-product>14-epimer of the end-product>starting subtance. The following chromatographic system is applied: adsorbent:

PF$_{254+366}$ Typ T. grade aluminum oxide; solvent: a 100:1 mixture of dichloromethane and methanol; eluting agent: a 20:4 mixture of dichloromethane and methanol. In this operation further 9 mg. of 3(S),14(S),16(S)-11-bromovincamine are obtained; thus the total yield of the product amounts to 37 mg. (39%).

As a second product, 7 mg. of 3(S),14(S),16(S)-11-bromo-14-epivincamine are isolated; m.p.: 136° C. (decomposition). This substance is obtained with a yield of 7.3%.

Mass spectrum: m/e (%)=432 (M+, 93), 431 (53.7), 414 (8.1), 386 (10), 372 (28.5), 330 (96.4).

EXAMPLE 9

(+)-3(S),17(S)-11-Bromo-14,15-dioxo-E-homo-eburnane 0.10 g. (0.22 mmoles) of 3(S),17(S)-11-bromo-14-oxo-15-hydroxyimino-E-homo-eburnane hydrochloride are treated in glacial acetic acid with p-toluenesulfonic acid and paraformaldehyde. The reaction is performed as described in Example 8. Having processed the reaction mixture 86 mg. of the crude product are obtained. The crude product is purified by preparative layer chromatography (adsorbent: silica gel Merck PF$_{254+366}$; running agent: a 8:2 mixture of dichloromethane and ether). The spot with higher R$_f$ value is eluted with ether. The pure (+)-3(S),17(S)-11-bromo-14,15-dioxo-E-homo-eburnane, isolated from the eluate, melts at 155°–156° C. (after recrystallization from ether).

$[\alpha]_D^{20} = +44°$ (c=1, in dichloromethane).

IR (in KBr pellets): 1710 (CO), 1690 (acid amide CO) cm$^{-1}$.

What we claim is:

1. An optically active or racemic 11-bromo-14,15-dioxo-E-homo-eburnane derivative of the formula (VII),

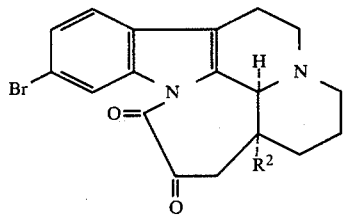

wherein R$^2$ is a C$_{1-6}$ alkyl group, or a pharmaceutically acceptable acid addition salt thereof.

2. An optically active or racemic 11-bromo-14-oxo-15-hydroxyimino-E-homo-eburnane derivative of the formula (VI),

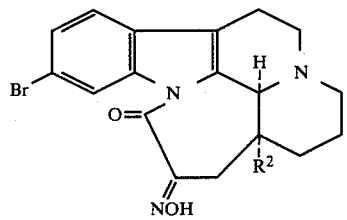

wherein R$^2$ is a C$_{1-6}$ alkyl group, or a pharmaceutically acceptable acid addition salt thereof.

3. An optically active brominated 14-oxo-E-homo-eburnane derivative of the formula (V),

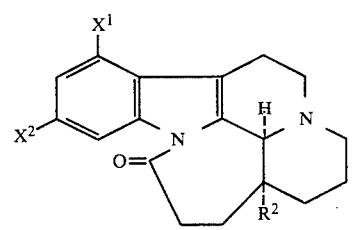

wherein X$^1$ is hydrogen and X$^2$ is bromine, or X$^1$ is bromine and X$^2$ is hydrogen, furthermore R$^2$ stands for a C$_{1-6}$ alkyl group, or a racemate or a pharmaceutically acceptable acid addition salt thereof.

4. An optically active 11-bromo-14-oxo-E-homo-eburnane derivative of the formula (Va),

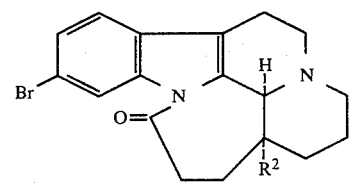

wherein R$^2$ is a C$_{1-6}$ alkyl group, or a racemate or a pharmaceutically acceptable acid addition salt thereof.

5. An optically active 9-bromo-14-oxo-E-homo-eburnane derivative of the formula (Vb),

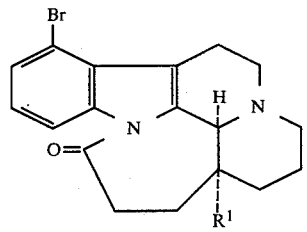

wherein R$^2$ is a C$_{1-6}$ alkyl group, or a racemate or a pharmaceutically acceptable acid addition salt thereof.

6. (±)-cis-11-Bromo-14,15-dioxo-E-homo-eburnane or a pharmaceutically acceptable acid addition salt thereof as defined in claim 1.

7. (±)-11-Bromo-14-oxo-15-hydroxyimino-E-homo-eburnane-(3αH,17αC$_2$H$_5$) or a pharmaceutically acceptable acid addition salt thereof as defined in claim 2.

8. 3(S),17(S)-11-Bromo-14-oxo-15-hydroxyimino-E-homo-eburnane or a pharmaceutically acceptable acid addition salt thereof as defined in claim 2.

9. (+)-3(S),17(S)-11-Bromo-14,15-dioxo-E-homo-eburnane or a pharmaceutically acceptable acid addition salt thereof as defined in claim 1.

10. 3(S),17(S)-11-Bromo-14-oxo-eburnane or a pharmaceutically acceptable acid addition salt thereof as defined in claim 3.

11. 3(S),17(S)-9-Bromo-14-oxo-E-homo-eburnane or a pharmaceutically acceptable acid addition salt thereof as defined in claim 3.

12. (±)-Cis-11-bromo-14-oxo-E-homo-eburnane-(3α,17α) or a pharmaceutically acceptable acid addition salt thereof as defined in claim 3.

13. (±)-Cis-9-bromo-14-oxo-E-homo-eburnane-(3α,17α) or a pharmaceutically acceptable acid addition salt thereof as defined in claim 3.

14. A process for the preparation of a racemic or optically active 11-bromo-vincaminic acid ester of the formula (I),

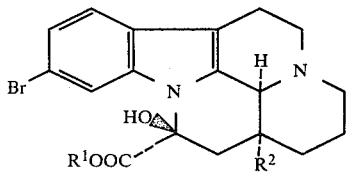

wherein $R^1$ and $R^2$ each represent a $C_{1-6}$ alkyl group, or a pharmaceutically acceptable acid addition salt thereof, characterized in that (a) an optically active or racemic 1-alkyl-1-alkoxycarbonylethyl-octahydroindoloquinolizine of the formula (II),

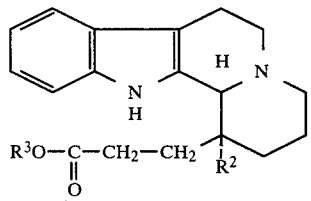

wherein $R^2$ is as defined above and $R^3$ stands for a $C_{1-6}$ alkyl group, or an acid addition salt thereof as treated with a brominating agent, the resulting mixture of the optically active or racemic 10-bromo- and 8-bromo-1-alkyl-1-alkoxycarbonylethyl-octahydroindoloquinolizine of the formulae (IIIa) and (IIIb)

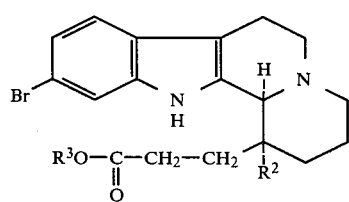

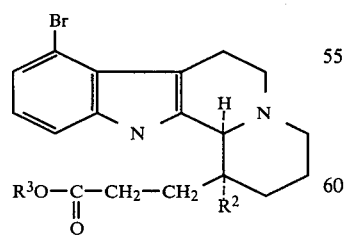

wherein $R^2$ and $R^3$ are as defined above, is treated with an alkaline agent, or (b) an optically active homoeburnane derivative of the formula (IV),

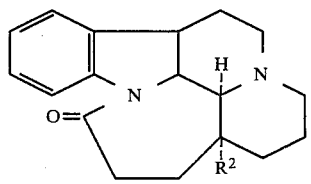

wherein $R^2$ is as defined above, or a racemate or salt thereof is treated with a brominating agent, and the 9-bromo- and 11-bromo compounds are separated from the resulting mixture of the optically active or recemic 11-bromo- and 9-bromo-14-oxo-E-homoeburnane derivatives of the formulae (Va) and (Vb),

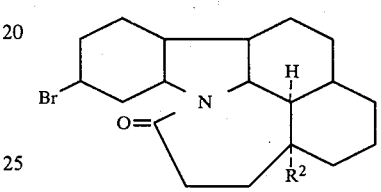

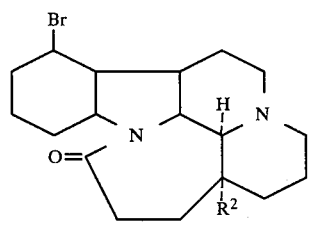

wherein $R^2$ is as defined above, or salts thereof, and the resulting racemic or optically active 11-bromo-14-oxo-E-homo-eburnane derivative of the formula (Va),

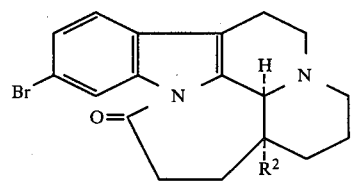

wherein $R^2$ is as defined above, or an acid addition salt thereof is reacted with a nitrosating agent, the resulting racemic or optically active 11-bromo-14-oxo-15-hydroxyimino-E-homo-eburnane derivative of the formula (VI),

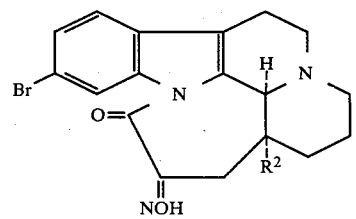

wherein $R^2$ is as defined above, or an acid addition salt thereof is subjected to deoxyimination, the resulting racemic or optically active 11-bromo- 14,15-dioxo-E-homo-eburnane derivative of the formula (VII),

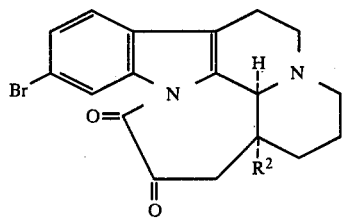

wherein $R^2$ is as defined above, or an acid addition salt thereof is treated with a base in an alcohol of the formula $R^1OH$, wherein $R^1$ is as defined above, and, if desired, the resulting 11-bromo-vincaminic acid ester of the formula (I) is converted into its pharmaceutically acceptable acid addition salt.

15. A process as claimed in claim 14, characterized in that elementary bromine is applied as brominating agent.

16. A process as claimed in claim 14, characterized in that bromination is performed in an apolar solvent, particularly in a halogenated hydrocarbon, in the presence of a Lewis acid.

17. A process as claimed in claim 14, characterized in that bromination is performed in a polar organic solvent.

18. A process as claimed in claim 14, characterized in that an alkali hydride or an alkali tert.-alkoxide is applied as alkaline agent in the treatment of the mixture of the compounds having the formulae (IIIa) and (IIIb).

19. A process as claimed in claim 14, characterized in that the compounds of the formulae (Va) and (Vb) are separated from each other by preparative layer chromatography.

20. A process as claimed in claim 14, characterized in that a racemic end-product of the formula (I) or any of the intermediates obtained in the above process is resolved into the optically active isomers.

21. A process as claimed in claim 14, characterized in that tert.-butyl nitrite is applied as nitrosating agent to nitrosate a racemic or optically active 11-bromo-14-oxo-E-homo-eburnane derivative of the formula (Va), and the reaction is performed in an inert organic solvent in the presence of an alkaline agent, preferably an alkali metal tert.-butoxide.

22. A process as claimed in claim 14, characterized in that a racemic or optically active 11-bromo-14-oxo-15-hydroxyimino-E-homo-eburnane derivative of the formula (VI) is deoxyiminated with an acid in the presence of a carbonyl compound.

23. A process as claimed in claim 14, characterized in that an alkali metal tert.-butoxide is applied as alkaline agent when contacting a racemic or optically active 11-bromo-14,15-dioxo-E-homo-eburnane derivative of the formula (VII) with an aliphatic alcohol of the formula $R^1OH$, wherein $R^1$ has the meaning as defined in claim 14.

24. A compound of the formula:

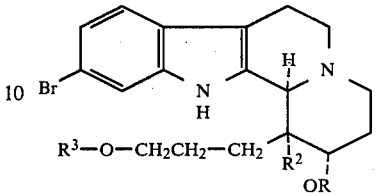

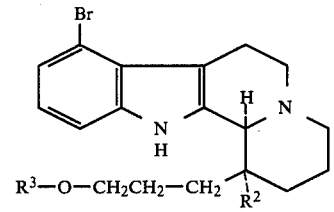

wherein $R^2$ and $R^3$ each represent a $C_1$ to $C_6$ alkyl, or a pharmaceutically acceptable salt thereof.

25. A method of protecting an animal against cerebral hypoxy which comprises the step of administering to the animal subject a pharmaceutically effective amount of the compound defined in claim 1 or a pharmaceutically acceptable salt thereof.

26. A method of protecting an animal against cerebral hypoxy which comprises the step of administering to the animal subject a pharmaceutically effective amount of the compound defined in claim 2 or a pharmaceutically acceptable salt thereof.

27. A method of protecting an animal against cerebral hypoxy which comprises the step of administering to the animal subject a pharmaceutically effective amount of the compound defined in claim 3 or a pharmaceutically acceptable salt thereof.

28. A method of protecting an animal against cerebral hypoxy which comprises the step of administering to the animal subject a pharmaceutically effective amount of the compound defined in claim 4 or a pharmaceutically acceptable salt thereof.

29. A method of protecting an animal against cerebral hypoxy which comprises the steps of administering to the animal subject a pharmaceutically effective amount of the compound defined in claim 5 or a pharmaceutically acceptable salt thereof.

30. A method of protecting an animal against cerebral hypoxy which comprises the step of administering to the animal subject a pharmaceutically effective amount of the compound defined in claim 24 or a pharmaceutically acceptable salt thereof.

* * * * *